United States Patent
Bostick et al.

(10) Patent No.: US 11,114,198 B2
(45) Date of Patent: Sep. 7, 2021

(54) MONITORING AN INDIVIDUAL'S CONDITION BASED ON MODELS GENERATED FROM E-TEXTILE BASED CLOTHING

(71) Applicant: INTERNATIONAL BUSINESS MACHINES CORPORATION, Armonk, NY (US)

(72) Inventors: James E. Bostick, Cedar Park, TX (US); John M. Ganci, Jr., Cary, NC (US); Martin G. Keen, Cary, NC (US); Sarbajit K. Rakshit, Kolkata (IN)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 422 days.

(21) Appl. No.: 15/845,348

(22) Filed: Dec. 18, 2017

(65) Prior Publication Data

US 2018/0294058 A1    Oct. 11, 2018

Related U.S. Application Data

(63) Continuation of application No. 15/482,889, filed on Apr. 10, 2017, now abandoned.

(51) Int. Cl.
*G16H 40/63*    (2018.01)
*G16H 15/00*    (2018.01)
(Continued)

(52) U.S. Cl.
CPC .............. *G16H 40/63* (2018.01); *G16H 10/60* (2018.01); *G16H 15/00* (2018.01); *G16H 50/20* (2018.01); *G16H 50/50* (2018.01)

(58) Field of Classification Search
CPC ........ G16H 40/63; G16H 50/50; G16H 10/60; G16H 15/00; G16H 50/20; G06F 19/3481; G06F 19/3418
See application file for complete search history.

(56) References Cited

U.S. PATENT DOCUMENTS

| 4,730,625 | A | * | 3/1988 | Fraser ................. A61B 5/1116 128/905 |
| 5,375,610 | A |   | 12/1994 | Lacourse et al. |

(Continued)

FOREIGN PATENT DOCUMENTS

| CN | 204654942 | 9/2015 |
| EP | 2191737 | 6/2010 |

(Continued)

OTHER PUBLICATIONS

Office Action from U.S. Appl. No. 15/482,889 dated Mar. 27, 2019, 23 pages.

(Continued)

*Primary Examiner* — Jonathan Durant
*Assistant Examiner* — Gregory D. Moseley
(74) *Attorney, Agent, or Firm* — Anthony England; Andrew D. Wright; Roberts Calderon Safran & Cole, P.C.

(57) ABSTRACT

Systems and methods for monitoring an individual's condition based on model generated from e-textile based clothing are described. A computer-implemented a method includes: obtaining, by a computer device, sensor data from an e-textile garment worn by a user; generating, by the computer device, a wireframe model of the user based on the sensor data; determining, by the computer device, a user activity; determining, by the computer device, a user condition based on the user activity and a the wireframe model; and automatically contacting, by the computer device, an (Continued)

assistance provider system based on determining the user condition warrants assistance.

16 Claims, 5 Drawing Sheets

(51) Int. Cl.
    *G16H 10/60*      (2018.01)
    *G16H 50/20*      (2018.01)
    *G16H 50/50*      (2018.01)

(56) References Cited

U.S. PATENT DOCUMENTS

| | | | |
|---|---|---|---|
| 8,165,844 | B2 | 4/2012 | Luinge et al. |
| 8,342,045 | B2 | 1/2013 | Maxwell et al. |
| 8,438,127 | B2 | 5/2013 | Kurata et al. |
| 8,551,030 | B2 | 10/2013 | Jenkins, III |
| 8,560,267 | B2 | 10/2013 | Jangle et al. |
| 8,749,391 | B2 | 6/2014 | Flinsenberg et al. |
| 8,876,738 | B1 | 11/2014 | Kahn et al. |
| 8,958,848 | B2 | 2/2015 | Shin et al. |
| 9,245,180 | B1 | 1/2016 | Hansen |
| 9,285,788 | B2 | 3/2016 | Nicoletti et al. |
| 9,492,084 | B2 | 11/2016 | Behar et al. |
| 9,588,582 | B2 | 3/2017 | Connor et al. |
| 9,681,827 | B2 | 6/2017 | Huang et al. |
| 10,105,076 | B2 | 10/2018 | Chu et al. |
| 2011/0066081 | A1* | 3/2011 | Goto .................. G16H 40/67 600/595 |
| 2011/0125064 | A1 | 5/2011 | Shyr |
| 2011/0213212 | A1 | 9/2011 | Al-Ali |
| 2011/0246123 | A1 | 10/2011 | DelloStritto et al. |
| 2012/0326873 | A1* | 12/2012 | Utter, II ............. A61B 5/1118 340/573.1 |
| 2013/0116514 | A1 | 5/2013 | Kroner et al. |
| 2014/0039274 | A1 | 2/2014 | Sarrafzadeh et al. |
| 2014/0350349 | A1 | 11/2014 | Geurts et al. |
| 2015/0164377 | A1* | 6/2015 | Nathan ............... A61B 5/1122 600/595 |
| 2015/0221202 | A1 | 8/2015 | Russell et al. |
| 2015/0269744 | A1 | 9/2015 | Mukheruee et al. |
| 2016/0007934 | A1 | 1/2016 | Arnold et al. |
| 2016/0071399 | A1 | 3/2016 | Altman et al. |
| 2016/0086500 | A1* | 3/2016 | Kaleal, III ............ G06Q 10/10 434/257 |
| 2016/0114213 | A1 | 4/2016 | Lee |
| 2016/0180222 | A1* | 6/2016 | Sierhuis ................ G06F 7/023 706/47 |
| 2016/0203691 | A1 | 7/2016 | Arnold et al. |
| 2016/0206242 | A1 | 7/2016 | Esposito et al. |
| 2016/0322078 | A1 | 11/2016 | Bose et al. |
| 2016/0338621 | A1* | 11/2016 | Kanchan ............. G16H 40/67 |
| 2017/0000384 | A1 | 1/2017 | Annegarn et al. |
| 2017/0036066 | A1* | 2/2017 | Chahine ............. A61B 5/4519 |
| 2017/0136265 | A1 | 5/2017 | Hyde et al. |
| 2017/0188895 | A1 | 7/2017 | Nathan |
| 2017/0238849 | A1 | 8/2017 | Chapman et al. |
| 2018/0008169 | A1 | 1/2018 | Chang |
| 2018/0049667 | A1 | 2/2018 | Heppe |
| 2018/0078192 | A1 | 3/2018 | Chen et al. |
| 2018/0113987 | A1 | 4/2018 | Zhu |
| 2018/0224273 | A1 | 8/2018 | Yamada et al. |

FOREIGN PATENT DOCUMENTS

| | | |
|---|---|---|
| EP | 2928369 | 10/2015 |
| WO | 2014/087266 | 6/2014 |
| WO | 2015/017712 | 2/2015 |

OTHER PUBLICATIONS

Tadano, S., Takeda, R., & Miyagawa, H. (2013). Three dimensional gait analysis using wearable acceleration and gyro sensors based on quaternion calculations. Sensors, 13(7), 9321-9343. (Year: 2013), 23 pages.

Tognetti, A., Lorussi, F., Bartalesi, R., Quaglini, S., Tesconi, M., Zupone, G., & De Rossi, D. (2005). Wearable kinesthetic system for capturing and classifying upper limb gesture in post-stroke rehabilitation. Journal of NeuroEngineering and Rehabilitation, 2(1 ), 8. (Year: 2005), 16 pages.

Veltink, P. H., & De Rossi, D. (2010). Wearable technology for biomechanics: e-textile or micromechanical sensors? [conversations in bme]. IEEE engineering in medicine and biology magazine, 29(3), 37-43. (Year: 2010), 7 pages.

Stoppa, M., & Chiolerio, A. (2014). Wearableelectronics and smart textiles: a critical review. sensors, 14(7), 11957-11992. (Year: 2014), 36 pages.

Bartalesi, R., Lorussi, F., Tesconi, M., Tognetti, A., Zupone, G., & De Rossi, D. (Mar. 2005). Wearable kinesthetic system for capturing and classifying upper limb gesture. In First Joint Eurohaptics Conference and Symposium . . . (Year: 2005), 2 pages.

Lorincz, K., Chen, B. R., Challen, G. W., Chowdhury, A. R., Patel, S., Bonato, P., & Welsh, M. (Nov. 2009). Mercury: a wearable sensor network platform for high-fidelity motion analysis. In SenSys (vol. 9, pp. 183-196). (Year: 2009), 15 pages.

Lorussi, F., Rocchia, W., Scilingo, E. P., Tognetti, A., & De Rossi, D. (2004). Wearable, redundant fabric-based sensor arrays for reconstruction of body segment posture. IEEE sensors Journal, 4(6), 807-818. (Year: 2004), 12 pages.

Mattmann, C., Amft, O., Harms, H., Traster, G., & Clemens, F. (Oct. 2007). Recognizing upper body postures using textile strain sensors. In 2007 11th IEEE international symposium on wearable computers (pp. 29-36). IEEE. (Year: 2007), 8 pages.

Hayward, "E-Textiles 2016-2026: Technologies, Markets and Players", http://www.idtechex.com/research/reports/e-textiles-2016-2026-technologies-markets-and-players-000459.asp, Feb. 19, 2016 , 5 Pages.

Azeem, "Electonric Textiles—Current Technologies and trend", http://www.academia.edu/3754440/Electronic_Textiles_-_Current_Technologies_and_trends, Academia.edu, accessed Apr. 6, 2017, 7 pages.

Bhattacharjee, "Electronic Textiles", http://www.slideshare.net/ttkbal/electronic-textiles, Jute and Fibre Technology, Apr. 8, 2013, 13 pages.

Edmison et al., "Using Piezoelectric Materials for Wearable Electronic Textiles", http://citeseerx.ist.psu.edu/viewdoc/download?doi=10.1.1.58.313&rep=rep1&type=pdf, Oct. 7-10, 2002, 8 pages.

Edmison et al., "An E-Textile System for Motion Analysis", NIH-PA Author Manuscript, 2004, 14 pages.

Einsmann et al., "Modeling a Wearable Full-body Motion Capture System", Proceedings of the 2005 Ninth IEEE International Symposium on Wearable Computers (ISWC'05), 2005, 8 pages.

ETextile Lounge—everything electronic and textiles, http://etextilelounge.com/, accessed Apr. 7, 2017, 22 pages.

Simmons, "A self-contained motion capture platform for e-textiles", Virginia Polytechnic Institute and State University, Aug. 13, 2010, 61 pages.

Cooper, "Your next smart shirt will make you look like an extra from 'Tron'", https://www.engadget.com/2015/01/06/cambridge-consultants-xelflex/, Jan. 6, 2015, 6 pages.

"Enflux Exercise Clothing: Improve Form! Real-time Analysis", https://www.kickstarter.com/projects/1850884998/enflux-smart-clothing-3d-workout-tracking-and-form, Kickstarter, accessed Dec. 19, 2016, 24 pages.

Heddoko, http://www.heddoko.com/ergonomics/, accessed Dec. 19, 2016, 4 pages.

List of IBM Patents or Patent Applications Treated as Related 1 page.

Specification "Monitoring an Individual's Condition Based on Models Generated From E-Textile Based Clothing" and Drawings in U.S. Appl. No. 15/482,889, filed Apr. 10, 2017, 38 pages.

Office Action from U.S. Appl. No. 15/482,889 dated Jan. 16, 2020, 32 pages.

(56) References Cited

OTHER PUBLICATIONS

Office Action from U.S. Appl. No. 15/482,889 dated Sep. 5, 2019, 39 pages.
Final Office Action from U.S. Appl. No. 15/482,889 dated Apr. 15, 2020, 22 pages.

* cited by examiner

FIG. 7

MONITORING AN INDIVIDUAL'S CONDITION BASED ON MODELS GENERATED FROM E-TEXTILE BASED CLOTHING

BACKGROUND

The present invention generally relates to monitoring an individual's condition based on a detected body position and, more particularly, to systems and methods for monitoring an individual's condition based on models generated from e-textile based clothing.

E-textiles, also known as smart garments, smart clothing, electronic textiles, smart textiles, or smart fabrics, are fabrics that enable digital components (including small computers), and electronics to be embedded in them. In e-textiles, one or more sensors may be embedded in the fabric of the garment. Additionally or alternatively, the fabric of the garment itself may be a sensor. The sensors employed in e-textiles may include, for example, a directional compass, one or more gyroscopes, one or more accelerometers, pressure gauges, strain gauges, temperature gauges, and fiber optics. The sensors employed in e-textiles may be used to monitor parameters of a user wearing the e-textile, such parameters including heart rate, respiration rate, skin temperature, and body position and movement. Specifically regarding body position and movement, e-textiles can be used to measure a user's full-body biomechanics in all planes of movement, joint angles, angular velocity, angular acceleration, and range of motion.

SUMMARY

In a first aspect of the invention, there is a method including: obtaining, by a computer device, sensor data from an e-textile garment worn by a user; generating, by the computer device, a wireframe model of the user based on the sensor data; determining, by the computer device, a user activity; determining, by the computer device, a user condition based on the user activity and a the wireframe model; and automatically contacting, by the computer device, an assistance provider system based on determining the user condition warrants assistance.

In another aspect of the invention, there is a system including an e-textile garment comprising sensors configured to detect a body position of a user wearing the e-textile garment; and a computer device comprising a processor and a memory. Program instructions stored in the memory and executed by the processor are configured to cause the computer device to: receive sensor data from the sensors of the e-textile garment; generate a model of the user wearing the e-textile garment based on the sensor data; determine a user activity; and determine a user condition based on the user activity and a the model.

In another aspect of the invention, there is a computer program product for monitoring a condition of a user. The computer program product includes a computer readable storage medium having program instructions embodied therewith. The program instructions are executable by a computer device to cause the computer device to: receive and store data defining body positions and movements associated with plural different activities; receive data of current body positions and movements of a user; determine a user activity from the plural different activities based on comparing the current body positions and movements of the user to the body positions and movements associated with the plural different activities; determine the user is in a first condition based on determining the current body positions and movements of the user are consistent with the body positions and movements associated with the determined user activity; determine the user is in a second condition based on determining the current body positions and movements of the user are inconsistent with the body positions and movements associated with the determined user activity for greater than a predefined amount of time; and automatically contact an assistance provider system based on determining the user is in the second condition.

BRIEF DESCRIPTION OF THE DRAWINGS

The present invention is described in the detailed description which follows, in reference to the noted plurality of drawings by way of non-limiting examples of exemplary embodiments of the present invention.

DETAILED DESCRIPTION

The present invention generally relates to monitoring an individual's condition based on a detected body position and, more particularly, to systems and methods for monitoring an individual's condition based on models generated from e-textile based clothing. Embodiments of the invention recognize that there are situations in which data from e-textile based clothing may be used to monitor the condition of an individual that has become ill, injured, is in danger, or is otherwise in need of assistance. Such situations may include, for example: a person living alone who has fallen and been injured in the fall; a hazardous work environment in which a person working alone may have fallen, become ill, or become immobilized; and a situation in which a person is alone and has been injured.

Aspects of the invention address these situations by: gathering data in real-time from e-textile clothing; generating a model of the user's body (e.g., a 3D wireframe model) based on the data from the e-textile clothing; determining a user state based on the model; determining an activity of the user based on cognitive analysis of activity data; and determining (e.g., predicting) a user condition based on comparing the determined user state to predefined user states associated with the determined activity. An assistance provider (e.g., public safety officer, medical first responder, family member, etc.) may be contacted based on the determined user condition. In this manner, implementations of the invention leverage data from e-textile based clothing to predict a user's physical condition, and automatically provide a message to an assistance provider based on the determined condition of the user.

Additional aspects of the invention are directed to using data from e-textile clothing to detect gestures made by a user wearing the e-textile clothing, and using the detected gestures to control functions of the user's mobile device. In this manner, a user that is alone and in need of assistance may use body gestures to control their mobile device to contact an assistance provider, even in situations when the user cannot reach or otherwise physically manipulate their mobile device.

Accordingly, in an exemplary implementation there is a method comprising: receiving a movement profile of a user, wherein the movement profile is obtained via sensors coupled to an e-textile clothing worn by the user and comprises a series of movements made by the user; generating a human wireframe model of the user based on the movement profile, the human wireframe model capturing the series of movements made by the user through the movement profile; and repeating the steps of receiving and generating to establish a movement baseline threshold of the user. The method may further comprise: detecting that a second series of movements deviate from the movement baseline threshold, the second series of movements obtained via the sensors coupled to the e-textile clothing worn by the user; and generating an alert indicative of said deviation. The method may further comprise: detecting a gesture of the user based on data from the e-textile clothing; and controlling at least one function of a mobile device of the user based on the detecting the gesture.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 1:
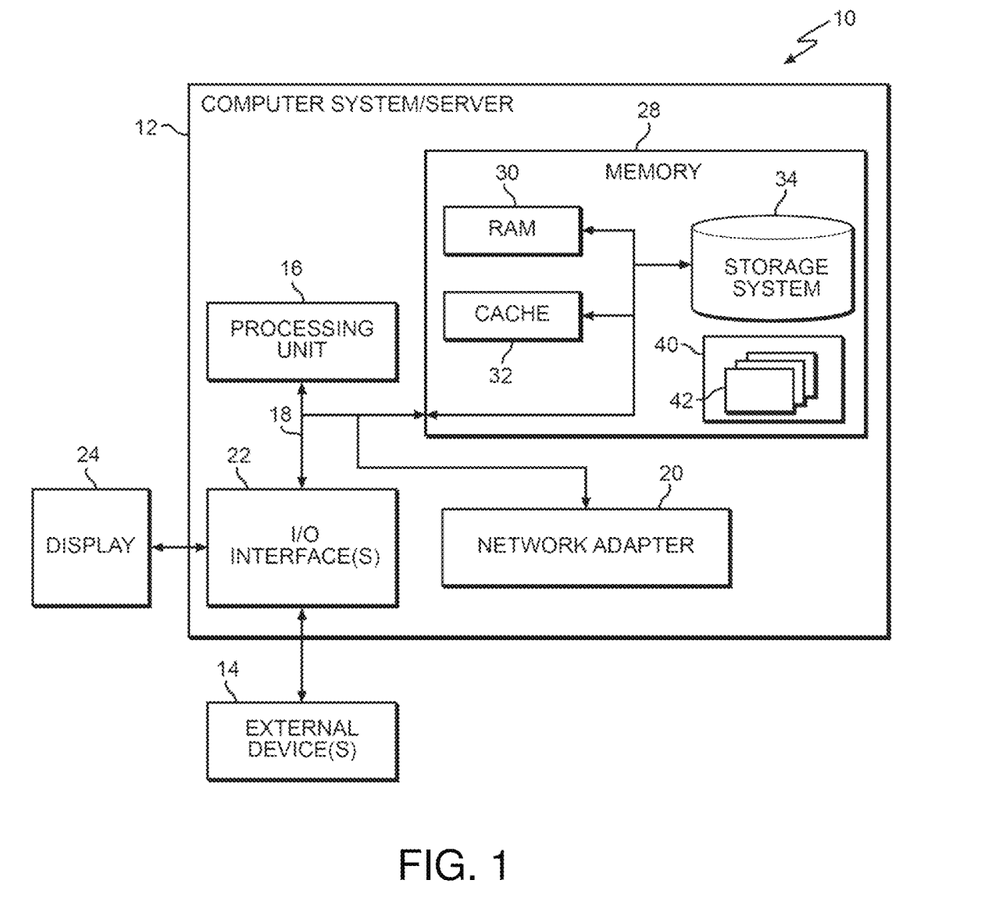
FIG. 1 depicts a computing infrastructure according to an embodiment of the present invention.

Referring now to FIG. 1, a schematic of an example of a computing infrastructure is shown. Computing infrastructure 10 is only one example of a suitable computing infrastructure and is not intended to suggest any limitation as to the scope of use or functionality of embodiments of the invention described herein. Regardless, computing infrastructure 10 is capable of being implemented and/or performing any of the functionality set forth hereinabove.

In computing infrastructure 10 there is a computer system (or server) 12, which is operational with numerous other general purpose or special purpose computing system environments or configurations. Examples of well-known computing systems, environments, and/or configurations that may be suitable for use with computer system 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system 12 may be described in the general context of computer system executable instructions, such as program modules, being executed by a computer system. Generally, program modules may include routines, programs, objects, components, logic, data structures, and so on that perform particular tasks or implement particular abstract data types. Computer system 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, computer system 12 in computing infrastructure 10 is shown in the form of a general-purpose computing device. The components of computer system 12 may include, but are not limited to, one or more processors or processing units (e.g., CPU) 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system 12 typically includes a variety of computer system readable media. Such media may be any available media that is accessible by computer system 12, and it includes both volatile and non-volatile media, removable and non-removable media.

System memory 28 can include computer system readable media in the form of volatile memory, such as random access memory (RAM) 30 and/or cache memory 32. Computer system 12 may further include other removable/non-removable, volatile/non-volatile computer system storage media. By way of example only, storage system 34 can be provided for reading from and writing to a nonremovable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system 12 may also communicate with one or more external devices 14 such as a keyboard, a pointing device, a display 24, etc.; one or more devices that enable a user to interact with computer system 12; and/or any devices (e.g., network card, modem, etc.) that enable computer system 12 to communicate with one or more other computing devices. Such communication can occur via Input/Output (I/O) interfaces 22. Still yet, computer system 12 can communicate with one or more networks such as a local area network (LAN), a general wide area network (WAN), and/or a public network (e.g., the Internet) via network adapter 20. As depicted, network adapter 20 communicates with the other components of computer system 12 via bus 18. It should be understood that although not shown, other hardware and/or software components could be used in conjunction with computer system 12. Examples, include, but are not limited to: microcode, device drivers, redundant processing units, external disk drive arrays, RAID systems, tape drives, and data archival storage systems, etc.

Figure 2:
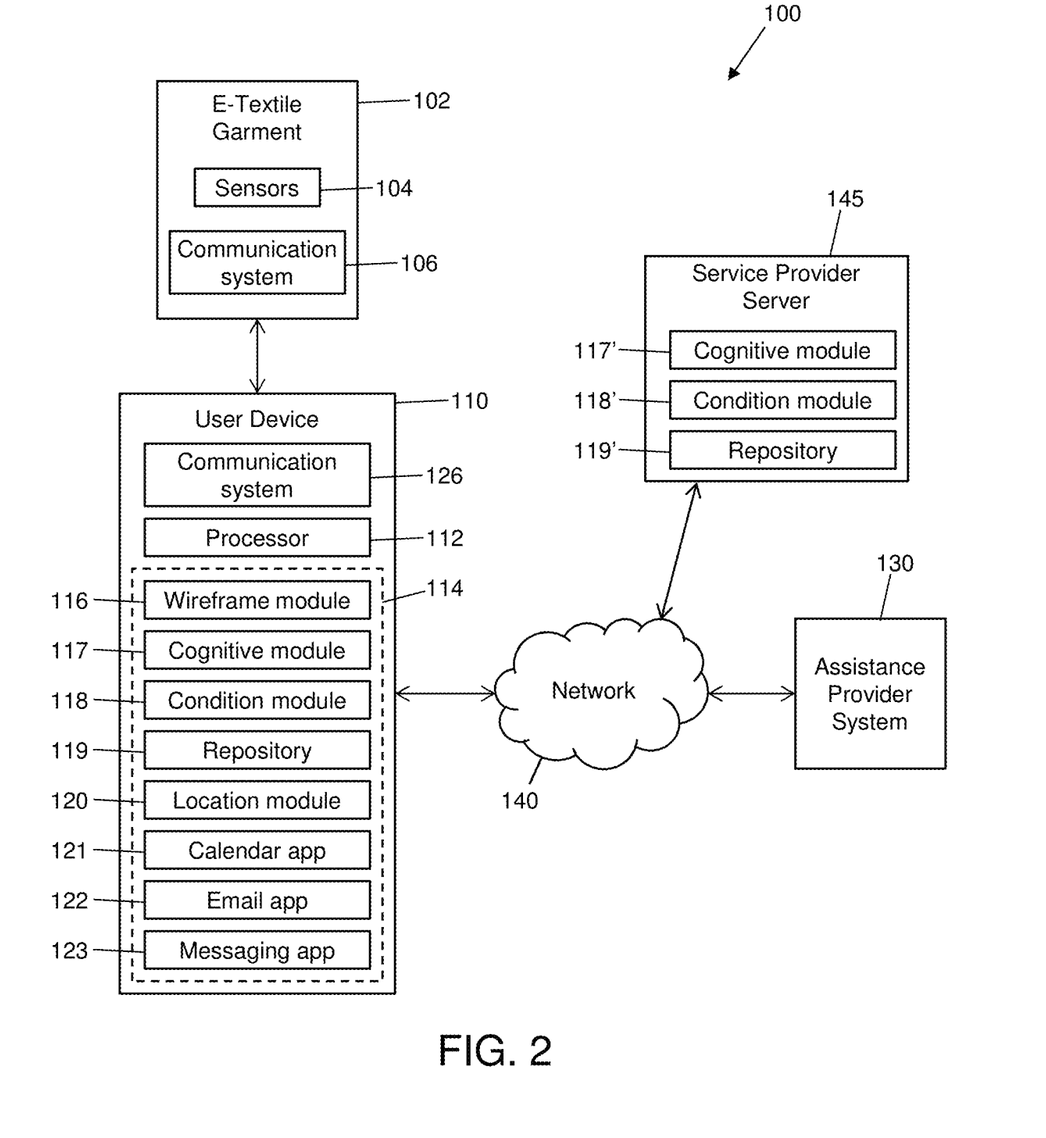
FIG. 2 shows an exemplary environment in accordance with aspects of the invention.

FIG. 2 shows an exemplary environment 100 in accordance with aspects of the invention. The environment includes at least one e-textile garment 102 including a plurality of sensors 104 and a communication system 106. The e-textile garment 102 may be any type of garment (e.g., clothing) or combination of plural garments including, for example, an upper body garment (e.g., shirt, sweater, jacket, etc.) and a lower body garment (e.g., long pants, short pants, etc.).

In embodiments, the sensors 104 may include one or more types of sensors that are configured to obtain data that is used in determining at least one of a body position and movement of a user wearing the e-textile garment 102. The sensors 104 may also include one or more sensors that obtain data that is used in determining at least one of a heart rate, respiration rate, and skin temperature of a user wearing the e-textile garment 102. For example, the sensors 104 may include at least one of: a compass; one or more gyroscopes; one or more accelerometers; pressure gauges; strain gauges; temperature gauges; and fiber optics. The sensors 104 may be embedded in a fabric of the e-textile garment 102 and/or may be integrated as part the fabric itself (e.g., threads made of electrically conductive material).

In an exemplary embodiment, the sensors 104 comprise electrically conductive threads that are woven in a predefined grid pattern of the fabric of the e-textile garment 102. In this exemplary embodiment, each of the sensors is identified uniquely and is connected to an e-textile thread circuit. In this manner, a relative position of each one of the sensors 104 is identified. In this exemplary embodiment, a computer device may receive a signal from each respective one of the sensors 104, and based on relative signal strengths the computer device may identify a relative position of each of the sensors 104 on real time basis. Implementations of the invention are not limited to this exemplary embodiment, and other types of sensors may be used as the sensors 104.

Still referring to FIG. 2, the environment 100 includes a user device 110 that communicates with the e-textile garment 102. The user device 110 is a computer device and may include one or more components of the computer system 12 of FIG. 1. For example, the user device 110 may include at least a processor 112 (e.g., similar to processing unit 16) and a memory 114 (e.g., similar to memory 28). In embodiments, the user device 110 is a mobile computer device such as a smartphone, tablet computer, or laptop computer. The user device 110 may be configured to communicate with the e-textile garment 102 via wired and/or wireless communication, and may be configured to communicate with one or more assistance provider systems 130 via a network 140 such as the Internet.

According to aspects of the invention, the user device 110 includes a wireframe module 116, a cognitive module 117, and a condition module 118, each of which may be one or more respective program modules 42 as described with respect to FIG. 1. In embodiments, the user device 110 also includes a repository 119 that stores activity data and movement data associated with the user wearing the e-textile garment 102. The user device may also include conventional program modules and/or application programs including but not limited to: a location module 120 (e.g., a global positioning system (GPS) location module that determines a GPS location of the user device 110); a calendar app 121; an email app 122; and a messaging app 123. In implementations, the user device 110 may include additional or fewer components than those shown in FIG. 2. In implementations, separate components may be integrated into a single computing component or module. Additionally, or alternatively, a single component may be implemented as multiple computing components or modules.

In accordance with aspects of the invention, the wireframe module 116 is configured to generate a model of the body position of the user wearing the e-textile garment 102 based on data from the sensors 104. In embodiments, the user device 110 obtains real-time data from the sensors 104 via communication between a communication system 106 of the e-textile garment 102 and a communication system 126 of the user device 110. The communication may be wired and/or wireless (e.g., Bluetooth, NFC, etc.). Based on the data received from the sensors 104, the wireframe module 116 is configured to generate a real-time 3D wireframe model of the body position of the user wearing the e-textile garment 102, as described in greater detail with respect to FIG. 3. In this manner, the body position and movements of the user wearing the e-textile garment 102 are detected and modeled in real time.

Figure 3:
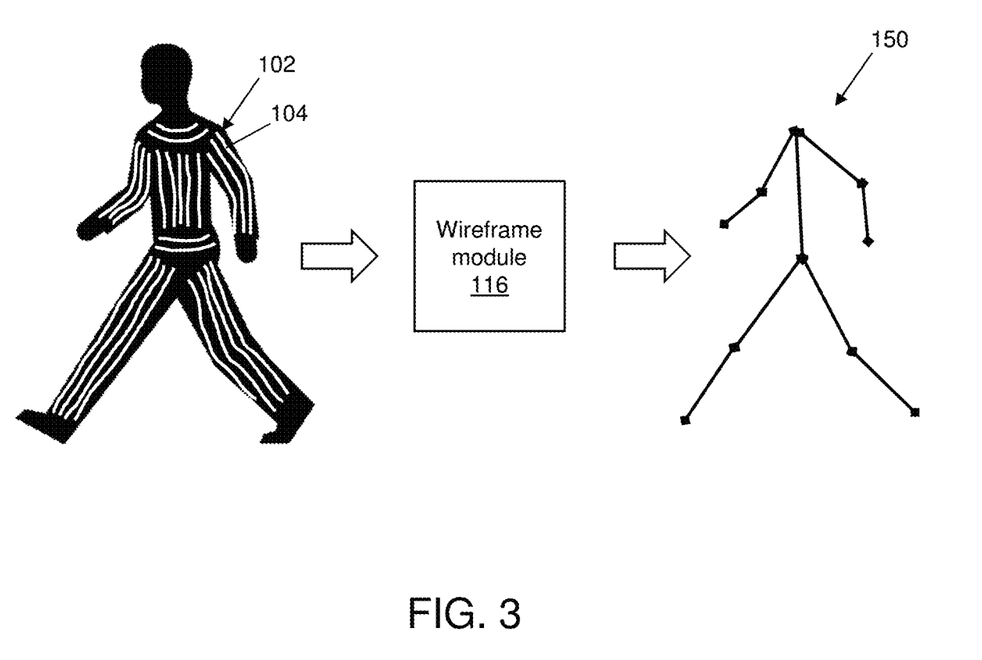
FIG. 3 illustrates generating a wireframe model in accordance with aspects of the invention.
Figure 4:
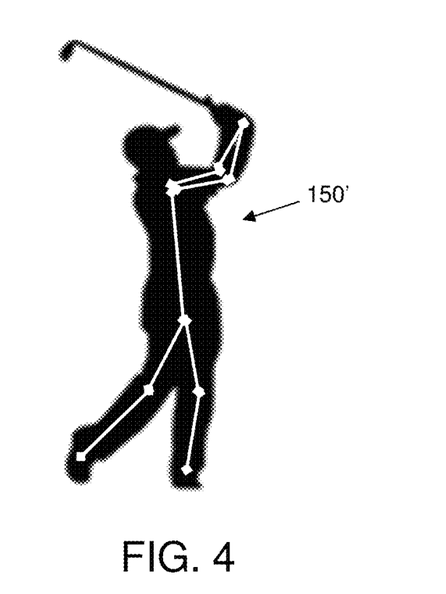
FIGS. 4-6 illustrate exemplary wireframe models in accordance with aspects of the invention.
Figure 5:
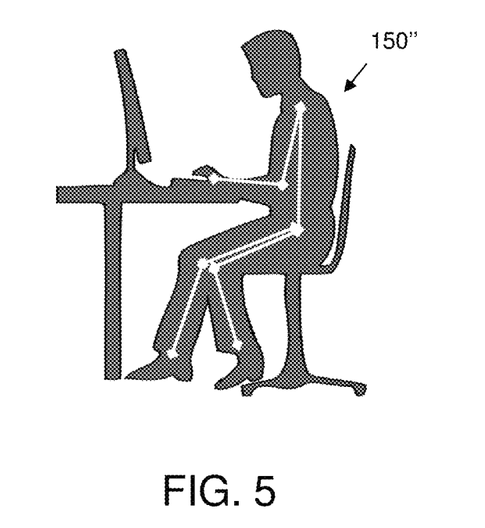
Figure 6:
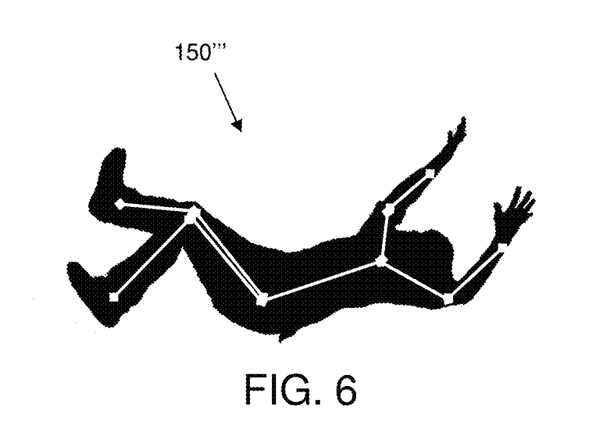

FIG. 3 shows an example of a wireframe model 150 generated by the wireframe module 116 based on data received by the sensors 104. As shown in FIG. 3, a user is wearing the e-textile garment 102 including the sensors 104 (diagrammatically shown as white lines on the e-textile garment 102.) In accordance with aspects of the invention, the wireframe module 116 receives data from the sensors 104 and generates the wireframe model 150 that corresponds to the real-time body position of the user wearing the e-textile garment 102. As the user's body position changes, the wireframe module 116 receives new data from the sensors 104 and generates a new wireframe model. FIGS. 4-6 depict examples of wireframe models generated in the same manner as that of FIG. 3. For example, FIG. 4 shows a wireframe model 150' of a user playing golf. FIG. 5 shows a wireframe model 150" of a user sitting at a desk. FIG. 6 shows a wireframe model 150''' of a user laying on the ground after a fall.

Referring back to FIG. 2, in accordance with aspects of the invention, the cognitive module 117 is configured to determine a user activity of the user wearing the e-textile garment 102 based on cognitive analysis of activity data, as described herein. In embodiments, the activity data includes data from at least one of: the repository 119; the location module 120; the calendar app 121; the email app 122; and the messaging app 123. For example, the cognitive module may determine that user is currently engaged in a particular activity (e.g., playing soccer) based on comparing the current (e.g., real time) body positions and movements of the user to historic body positions and movements defined by data stored in the repository 119. In this example, the repository 119 may store data that defines historic body positions and movements of this user for plural different activities (e.g., playing soccer, at work, etc.), and the cognitive module 117 may compare the user's currently detected body positions and movements to the historic body positions and movements, and may determine a best match of one of the plural different activities based on the comparing.

In embodiments, the user may train the cognitive module 117 by inputting an indication of an activity (e.g., playing soccer) while being engaged in the activity and wearing the e-textile garment 102. In this training implementation, the system may detect the user's body positions and movements during the indicated activity, and save this data in the repository 119, i.e., as historic data of body positions and movements associated with the indicated activity. The historic data can then later be used in future comparisons when determining the user's activity.

The cognitive module 117 may also utilize data from one or more of the location module 120, the calendar app 121, the email app 122, and the messaging app 123 when determining the user activity. For example, data from the location module 120 may be used to determine that the user wearing the e-textile garment 102 is at a location associated with a particular activity (e.g., at a soccer field, at work, etc.). As another example, data from the calendar app 121 may be used to determine that the user wearing the e-textile garment 102 is currently scheduled to be engaged in a particular activity (e.g., soccer game, meeting in the conference room, etc.). As another example, data from the email app 122 and/or the messaging app 123 may be used to determine that the user wearing the e-textile garment 102 is currently engaged in a particular activity (e.g., playing soccer, working, etc.). In embodiments, the cognitive module 117 leverages insights determined from one or more of these sources 120-123, in conjunction with comparing the current (e.g., real time) body positions and movements of the user to historic body positions and movements defined in the repository 119, to determine a user activity in which the user wearing the e-textile garment 102 is currently engaged.

In accordance with aspects of the invention, the condition module 118 is configured to determine (e.g., predict) a user condition of the user wearing the e-textile garment 102 based on the determined user activity and a user current state. In one embodiment, the user condition is determined to be one of normal and distressed, although implementations of the invention are not limited to these two conditions and other user conditions may be employed. As used herein, the user current state is a body position and/or movement of the user determined by the wireframe module 116, e.g., as shown in FIGS. 4-6. In embodiments, the condition module 118 compares the user current state (i.e., the user's current body position and/or movement) to the user's historic body positions and movements for the determined user activity as defined in the repository 119. The comparing may comprise the condition module 118 comparing (i) data that defines the 3D wireframe models for the user current state to (ii) data that defines the 3D wireframe models for historic body positions to movements for the determined user activity. Based on the comparing, the condition module 118 determines that the user's condition is one of a first condition (e.g., normal) and a second condition (e.g., distressed).

In aspects, the comparing includes determining spatial deviations of positions of body parts (e.g., arms, legs, torso, head) between the model of the user current state and the models of historic body positions and movements. For example, the comparing may include determining spatial deviations of positions of body parts (e.g., arms, legs, torso, head) between a wireframe model of the user current state to wireframe models of the historic body positions and movements for the determined user activity. Configurable thresholds may be used to define how much of a deviation is permissible between the user current state and the historic body positions and movements, i.e., for the purpose of determining whether the user current state is deemed consistent or inconsistent with the historic body positions and movements for the determined user activity.

For example, the determined user activity may be 'exercising', and the determined user current state may be laying prone. In this example, the condition module 118 compares the wireframe model of the user current state (i.e., laying prone) to the wireframe models of the historic body positions and movements for the determined user activity (i.e., exercising). Based on this comparing, the condition module 118 determines that the user current state is consistent with historic body positions and movements for the determined user activity, and determines that the user condition is normal.

In another example, the determined user activity may be 'playing golf', and the determined user current state may be laying prone. In this example, the condition module 118 compares the wireframe model of the user current state (i.e., laying prone) to the wireframe models of the historic body positions and movements for the determined user activity (i.e., playing golf). Based on this comparing, the condition module 118 determines that the user current state is inconsistent with historic body positions and movements for the determined user activity, and determines that the user condition is distressed.

In addition to comparing the user current state to the user's historic body positions and movements for the determined user activity, the condition module 118 may also be configured to compare the user current state to predefined distress body positions and movements. For example, the repository 119 may store data defining predefined distress body positions and movements such as choking, heart attack, etc. The data defining the predefined distress body positions and movements may be 3D wireframe model data that can be compared to the user current state wireframe model data in the manner already described herein. In the event that the condition module 118 determines that the user current state is consistent with one of the predefined distress body positions and movements, then the condition module 118 determines that the user condition is distressed.

In embodiments, the condition module 118 may be configured to determine the user condition (e.g., normal or distressed) based in part on an amount of time that the user current state is inconsistent with historic body positions and movements for the determined user activity. Aspects of the invention envision situations in which the user current state is inconsistent with historic body positions and movements for the determined user activity, but the deviation is for a short amount of time and, thus, may not be indicative of a distressed state. For example, a user may trip and fall down without injury, and then stand back up after the fall. In this example, the user current state may deviate significantly from historic body positions and movements for the determined user activity, but the deviation is only for a relatively short amount of time. Accordingly, in embodiments the condition module 118 measures an amount of time that the user current state is inconsistent with historic body positions and movements for the determined user activity, and compares the measured amount of time to a time threshold value. If the measured amount of time is less than the time threshold value, then the condition module 118 determines the user condition as normal. If the measured amount of time is greater than the time threshold value, then the condition module 118 determines the user condition as distressed.

In embodiments, the condition module 118 may be configured to determine the user condition (e.g., normal or distressed) based in part on an amount of time that the user current state is consistent with a predefined distress body position or movement. For example, a user may move their hands to their throat for a short amount of time (e.g., for a reason other than to make a choking gesture), and then may move their hands away from their throat. Accordingly, in embodiments the condition module 118 measures an amount of time that the user current state is consistent with a predefined distress body position or movement, and compares the measured amount of time to the time threshold value. If the measured amount of time is less than the time threshold value, then the condition module 118 determines the user condition as normal. If the measured amount of time is greater than the time threshold value, then the condition module 118 determines the user condition as distressed.

In embodiments, the condition module 118 may be configured to automatically adjust the time threshold value (against which the measured amount of time is compared) based on detecting a combination of different states of the user. For example, a user experiencing a heart attack may make a first gesture of clutching their chest (e.g., a first user current state), and then may fall to the ground (e.g., a second user current state). In this example, the system detects that the first user current state of clutching their chest is consistent with a predefined distress body position or movement, and that the second user current state of falling down is inconsistent with historic body positions and movements for the determined user activity. Accordingly, in embodiments the condition module 118 reduces the time threshold value by a predefined amount (e.g., 50%, 60%, 70%, 80%, etc.) when the system detects that the user current state satisfies more than one criteria for indicating distress.

In embodiments, the condition module 118 may be configured to determine the user condition (e.g., normal or distressed) based in part on biometric data obtained from the sensors 104 of the e-textile garment 102. For example, the sensors 104 may include at least one biometric sensor that detects the user's heart rate concurrently with other ones of the sensors 104 detecting the user's body position and movements. The condition module 118 may be configured to compare the detected biometric data (e.g., the user's current heart rate) to a biometric threshold value (e.g., a threshold heart rate). The condition module 118 may be configured to reduce the time threshold value (against which the measured amount of time is compared) by a predefined amount (e.g., 50%, 60%, 70%, 80%, etc.) based on determining that the detected biometric data (e.g., the user's current heart rate) exceeds the biometric threshold value (e.g., a threshold heart rate).

Still referring to FIG. 2, in embodiments the condition module 118 is configured to send a message to at least one assistance provider system 130 based on determining that the user's condition is distressed. The assistance provider system 130 may be a computer device and/or telephone system of a public safety officer, medical first responder, primary care physician, family member, etc. The message may be of any desired format including but not limited to an automated telephone call, email, text message, etc. The message may include an identity of the user and a GPS location of the user. The message may include an indication that the user is distressed and needs assistance. Depending on the determined user condition, the message may be sent to one of plural different assistance provider systems. For example, a first type of determined user condition may result in a message being sent to the first assistance provider system (e.g., that of a family member), and a second type of determined user condition may result in a message being sent to the second assistance provider system (e.g., that of a medical first responder).

In accordance with aspects of the invention, the user device 110 is configured to, based on determining the user condition is distressed, detect a gesture of the user wearing the e-textile garment 102 and control at least one function of the user device 110 of the user based on the detecting the gesture. In embodiments, the repository 119 stores data that defines at least one gesture. The data defining the gesture may be 3D wireframe model data as described herein. The repository 119 stores data that defines the gesture as being associated with a function of the user device 110, such as locking, unlocking, enabling a specific function, security, etc. In this manner, the condition module 118 may be configured to control the associated function of the user device 110 based on determining the user is in a distressed state and detecting the gesture associated with the function.

For example, the repository 119 may store data that defines a gesture as a waving motion with the right arm. The repository 119 may also store data that associates this gesture with the function of initiating voice activated control of a telephone function of the user device 110. In this example, when the condition module 118 determines the user's condition as distressed and detects the gesture (i.e., the user waving their right arm), then the condition module 118 controls the user device 110 to initiate voice activated control of the telephone function of the user device 110. In this manner, the user wearing the e-textile clothing 102 may control functions of their user device 110, e.g., to call for assistance, even when the user cannot physically manipulate the user device 110. This is useful when the user is incapacitated to the extent that they cannot reach or physically manipulate the user device 110.

Plural different gestures may be defined in the repository 119, and each different gesture may be associated with a different function of the user device 110. In embodiments, the system detects that the user has made a predefined gesture by: detecting the user's movement using the sensors 104; modeling the user's detected movement using the wireframe module 116; and comparing the modeled movement to the data in the repository 119 that defines the one or more gestures.

As shown in FIG. 2, at least one of the cognitive module, the condition module, and the repository may reside at a service provider server 145 (as indicated by cognitive module 117', condition module 118', and repository 119') instead of on the user device 110. In this implementation, the user device 110 generates the wireframe model based on the sensor data and communicates the wireframe model to the service provider server 145 via the network 140.

Figure 7:
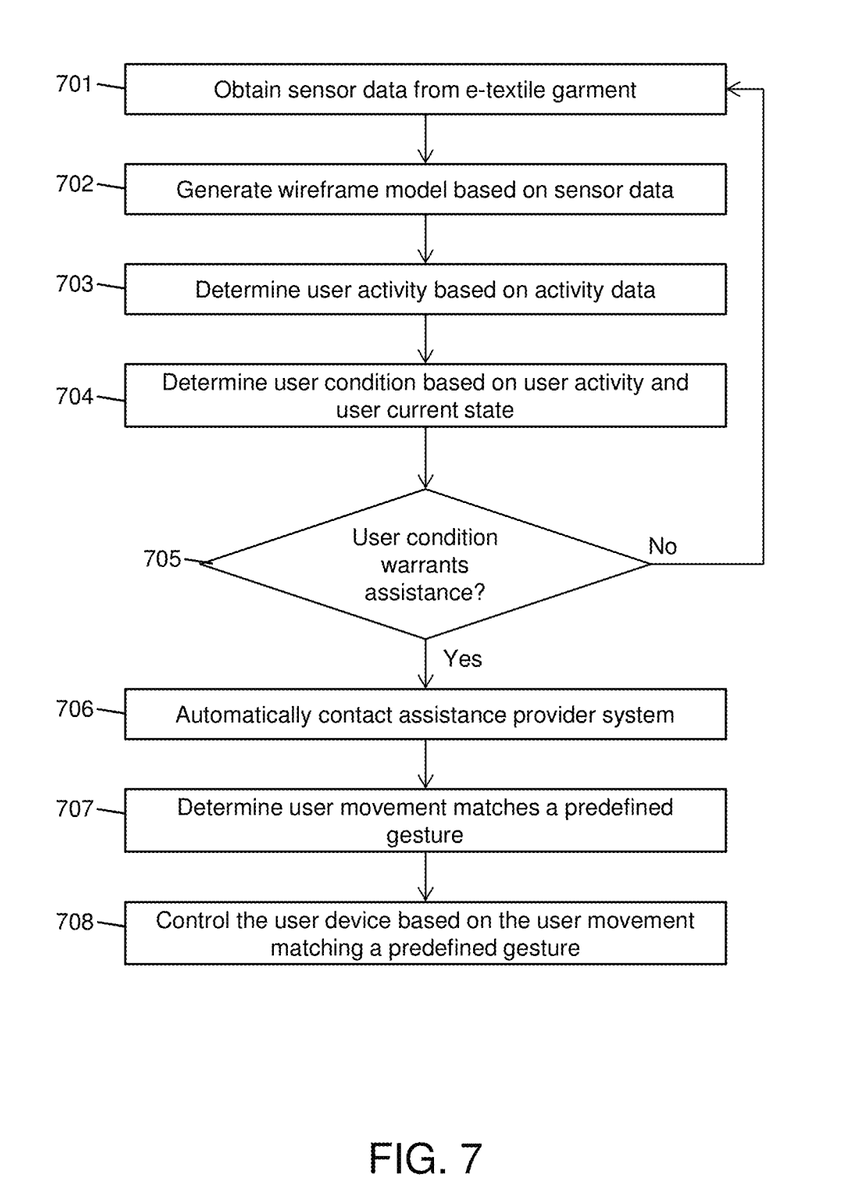
FIG. 7 shows a flowchart of a method in accordance with aspects of the invention.

FIG. 7 shows a flowchart of methods in accordance with aspects of the invention. Steps of the method of FIG. 7 may be performed in the environment illustrated in FIG. 2 and are described with reference to elements and steps described with respect to FIG. 2.

At step 701, the system obtains sensor data from an e-textile garment. In embodiments, and as described with respect to FIG. 2, the user device 110 receives data from sensors 104 of an e-textile garment 102 being worn by a user.

At step 702, the system generates a wireframe model based on the sensor data from step 701. In embodiments, and as described with respect to FIGS. 2 and 3, the wireframe module 116 of the user device 110 generates a 3D wireframe model of the user's body position and/or movements based on the data received from the sensors 104.

At step 703, the system determines a user activity based on activity data. In embodiments, and as described with respect to FIG. 2, the cognitive module 117 compares the wire frame model of the user's current body position and/or movements to wireframe models of historic body positions and movements associated with different activities, and determines a current user activity based on the comparing. The cognitive module 117 may also determine insights by analyzing data from at least one of the location module 120, the calendar app 121, the email app 122, and the messaging app 123. The cognitive module 117 may use the insights in determining the current user activity.

At step 704, the system determines a user condition based on the user activity and the user state. In embodiments, and as described with respect to FIG. 2, the condition module 118 determines whether the user current state is consistent with or inconsistent with the user's historic body positions and movements associated with the determined user activity. Step 704 may also include the condition module 118 determining whether the user current state is consistent with or inconsistent with predefined distress body positions and movements, as described with respect to FIG. 2. Step 704 may include the condition module 118 comparing a time to a time threshold, and may include automatically adjusting the time threshold based on predefined conditions being met, as described with respect to FIG. 2. In embodiments the condition module 118 determines the user condition as being one of a first condition (e.g., normal) and a second condition (e.g., distressed).

At step 705, the system determines whether the user condition (determined at step 704) warrants assistance. In embodiments, and as described with respect to FIG. 2, the condition module 118 may be programmed to determine that the first condition (e.g., normal) does not warrant assistance and that the second condition (e.g., distressed) does warrant assistance.

In the event the user condition does not warrant assistance, then the method returns to step 701 to continue the real-time monitoring. In the event the user condition warrants assistance, then at step 706 the system automatically contacts an assistance provider system. In embodiments, and as described with respect to FIG. 2, the condition module 118 sends a message to an assistance provider system 140 based on the determining the user condition is distressed.

At step 707, the system determines that a user movement matches predefined gesture. In embodiments, and as described with respect to FIG. 2, step 707 includes: detecting the user's movement using the sensors 104; modeling the user's detected movement using the wireframe module 116; and comparing the modeled movement to the data in the repository 119 that defines one or more gestures.

At step 708, the system controls a function of the user device 110 based on the determining the user movement matches a predefined gesture. In embodiments, and as described with respect to FIG. 2, the condition module 118 controls a function of the user device 110 that is defined as being associated with the gesture of step 707. The function may be, for example, unlocking the user device 110 and initiating voice activation of a telephone call.

In embodiments, a service provider could offer to perform the processes described herein. In this case, the service provider can create, maintain, deploy, support, etc., the computer infrastructure that performs the process steps of the invention for one or more customers. These customers may be, for example, any business that uses technology. In return, the service provider can receive payment from the customer(s) under a subscription and/or fee agreement and/or the service provider can receive payment from the sale of advertising content to one or more third parties.

In still additional embodiments, the invention provides a computer-implemented method. In this case, a computer infrastructure, such as computer system 12 (FIG. 1), can be provided and one or more systems for performing the processes of the invention can be obtained (e.g., created, purchased, used, modified, etc.) and deployed to the computer infrastructure. To this extent, the deployment of a system can comprise one or more of: (1) installing program code on a computing device, such as computer system 12 (as shown in FIG. 1), from a computer-readable medium; (2) adding one or more computing devices to the computer infrastructure; and (3) incorporating and/or modifying one or more existing systems of the computer infrastructure to enable the computer infrastructure to perform the processes of the invention.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer implemented method, comprising:
    obtaining, by a computer device, real-time sensor data from a remote e-textile garment worn by a user;
    generating, by the computer device, a real-time three-dimensional wireframe model of a current state of the user based on the real-time sensor data;
    determining, by the computer device, a user activity;
    determining, by the computing device, a first state of the user based on the real-time sensor data;
    determining, by the computing device, a second state of the user based on the real-time sensor data;
    determining, by the computing device, that a combination of the first state of the user and the second state of the user meets a predetermined rule;
    adjusting, by the computing device, a threshold time period associated with a user condition based on the determining that the combination of the first state of the user and the second state of the user meets the predetermined rule, thereby providing an adjusted threshold time period;
    determining, by the computer device, the user condition of the user based on spatial deviations between positions of body parts of the real-time three-dimensional wireframe model of the current state of the user and positions of body portions of the historic three-dimensional wireframe models associated with the user activity meeting predetermined threshold values for the adjusted threshold time period; and
    automatically contacting, by the computer device, an assistance provider system based on determining the user condition warrants assistance;
    wherein the determining the user condition comprises determining a user current state is a body position or movement that is consistent with a predefined distress body position or movement for greater than the adjusted threshold time period.

2. The method of claim 1, wherein the real-time three-dimensional wireframe model is a model of a body position of the user wearing the e-textile garment.

3. The method of claim 1, wherein the determining the user activity comprises comparing the real-time three-dimensional wireframe model to models of historic body positions and movements associated with plural activities.

4. The method of claim 3, wherein the determining the user activity is additionally based on a cognitive analysis of at least one from a group consisting of: location module data; calendar app data; email app data; and messaging app data.

5. The method of claim 1, wherein the determining the user condition comprises determining the user current state is one of consistent with or inconsistent with historic body positions and movements associated with the determined user activity.

6. The method of claim 1, wherein the determining the user condition comprises determining the first state of the user based on a first gesture of the user and the second state of the user based on a body position or movement of the user.

7. The method of claim 1, wherein adjusting the threshold time period comprises automatically adjusting the threshold time period by a predetermined percentage amount.

8. The method of claim 1, further comprising:
determining a movement of the user matches a predefined gesture; and
controlling a function of a user device based on the determining the movement of the user matches the predefined gesture.

9. The method of claim 1, further comprising:
receiving, by the computer device, an indication of an activity for a training session of the computer device;
determining, by the computer device, the user's body positions and movement during the activity based on sensor data from the remote e-textile garment worn by the user;
saving, by the computer device, activity data resulting from the determining the user's body positions and movements in a repository.

10. The method of claim 1, further comprising obtaining, by the computer device, user data from an email application of the computer device, the user data providing insights into the user activity, wherein the determining the user activity is based on movements of the user determined from the real-time three-dimensional wireframe model, the user data, and historic body position and movement data in a database.

11. The method of claim 1, wherein the determining the user activity comprises determining a best match of the real-time three-dimensional wireframe model and one of the historic three-dimensional wireframe models associated with the user activity.

12. The method of claim 1, wherein the real-time sensor data is obtained from sensors of the e-textile garment comprising electrically conductive threads woven in a predefined grid pattern of fabric of the e-textile garment.

13. The method of claim 1, wherein the first state is based on detecting biometric data of the user meets a biometric threshold value.

14. The method of claim 1, wherein the user condition indicates distress of the user.

15. The method of claim 1, further comprising:
determining, by the computer device, a movement of the user matches a predefined gesture; and
initiating, by the computer device, voice activated control of the computer device based on the determining the movement of the user matches the predefined gesture and based on the user condition.

16. The method of claim 1, further comprising: accessing, by the computer device, the historic three-dimensional wireframe models associated with the user activity stored in a database based on the user activity.

* * * * *